United States Patent [19]

Houston

[11] 4,392,237
[45] Jul. 5, 1983

[54] SCANNING X-RAY INSPECTION SYSTEM

[75] Inventor: John M. Houston, Schenectady, N.Y.

[73] Assignee: General Electric Company, Schenectady, N.Y.

[21] Appl. No.: 181,161

[22] Filed: Aug. 25, 1980

[51] Int. Cl.³ .............................................. G01N 23/00
[52] U.S. Cl. .................... 378/51; 250/358.1; 250/359.1; 250/385; 378/57
[58] Field of Search ............... 250/312, 374, 358 R, 250/359, 360, 385, 445 T; 378/51, 57

[56] References Cited

U.S. PATENT DOCUMENTS

| | | | |
|---|---|---|---|
| 3,808,444 | 4/1974 | Schneeberger et al. | 250/358 R X |
| 4,031,396 | 6/1977 | Whetten et al. | 250/385 |
| 4,047,041 | 9/1977 | Houston | 250/385 |
| 4,122,346 | 10/1978 | Enge | 250/398 |
| 4,135,095 | 1/1979 | Watanabe | 250/445 T |

Primary Examiner—Davis L. Willis
Attorney, Agent, or Firm—Lawrence D. Cutter; James C. Davis, Jr.; Marvin Snyder

[57] ABSTRACT

An x-ray fan beam is caused to impinge upon an object, such as airport luggage or jars of food, as the object moves translationally through the fan beam; after passage through the object, the x-rays are made to impinge upon an x-ray transmissive detector housing containing a gaseous detecting medium, a power electrode and a plurality of signal electrodes. The power electrode and the signal electrode are maintained at different voltage levels so that electrons and/or ions generated by the interaction of the gaseous detecting medium and the x-rays, drift toward the electrodes thereby producing an electrical current which can be sensed, analyzed, and used, for example, to generate an image or to indicate the presence of foreign matter.

10 Claims, 9 Drawing Figures

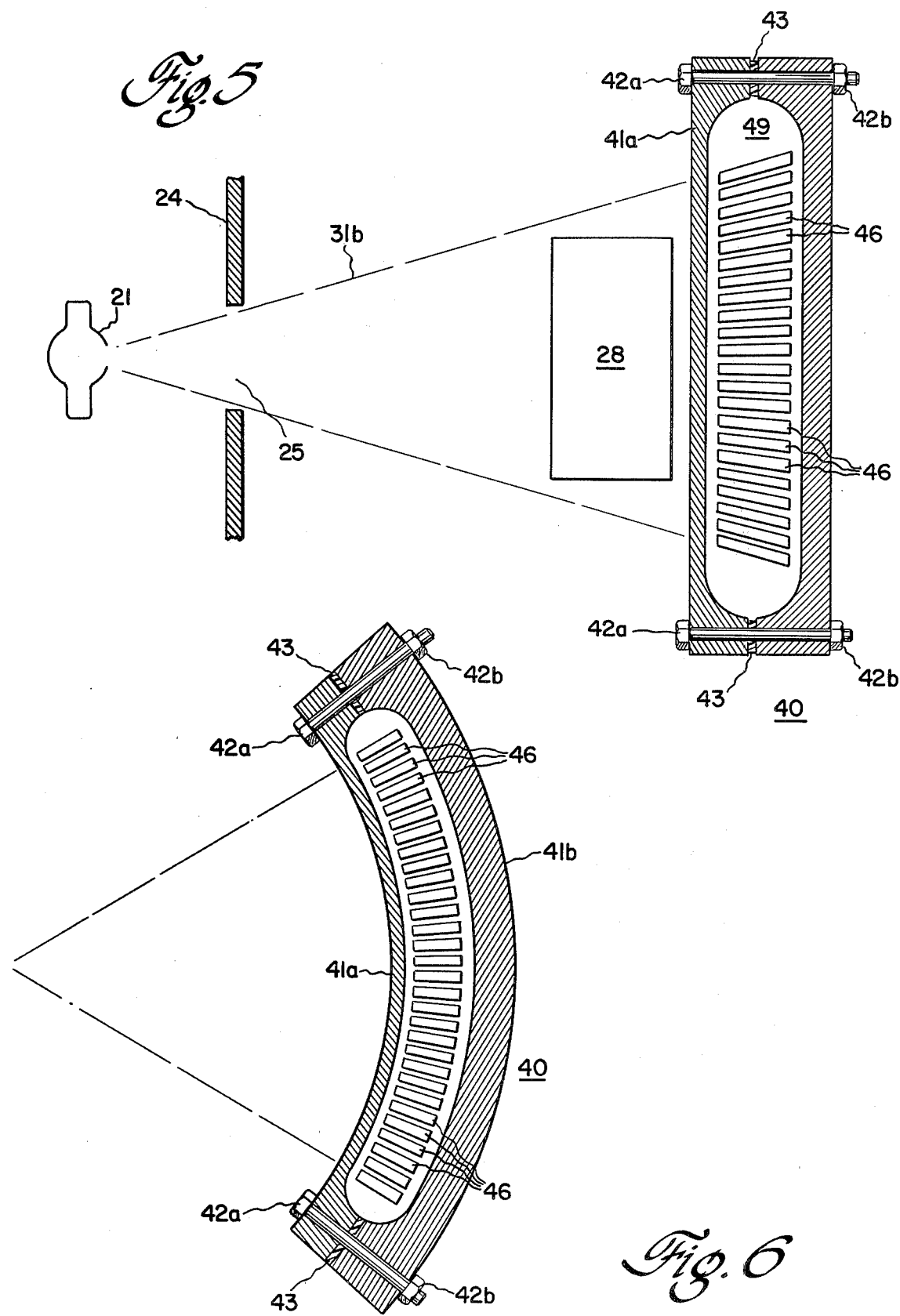

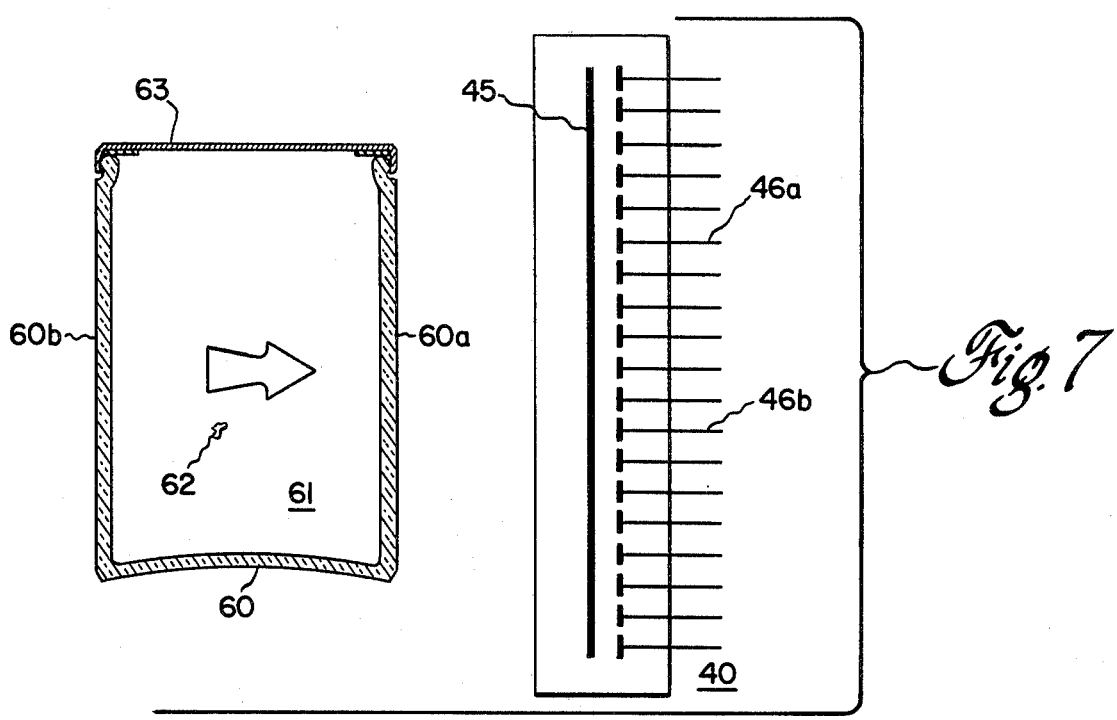
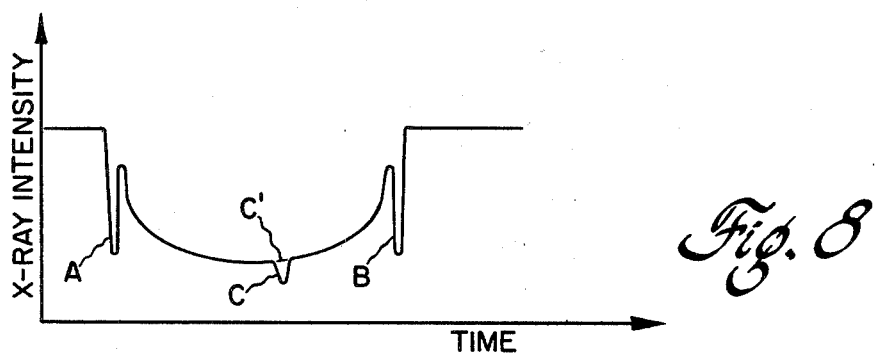
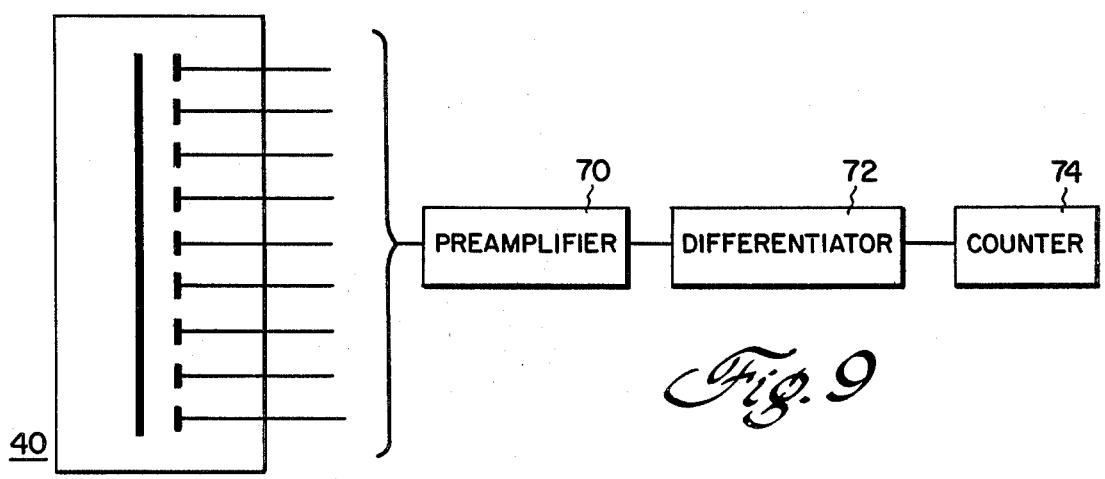

SCANNING X-RAY INSPECTION SYSTEM

BACKGROUND OF THE INVENTION

This invention relates to x-ray systems, and more particularly to x-ray systems employing xenon detectors configured so as to be especially useful as airport luggage inspection devices or as foreign matter detection devices.

Fan beam x-ray systems employing gaseous medium detectors have most recently been employed in computerized tomography radiographic imaging systems which produce a shadow-free image of the internal structure lying in an imaginary plane passing through the patient being studied. These computerized tomographic imaging systems often employ gaseous medium detectors such as the xenon detectors described in U.S. Pat. No. 4,047,041 issued Sept. 6, 1977 to the applicant herein and assigned to the same assignee as this invention, which patent is hereby incorporated herein by reference. In these computerized tomography systems the x-ray fan beam is typically approximately 1 cm thick. In such systems, x-ray dosage received by the patient is a highly significant consideration in the structuring of the detector system as is the resolution sought to be achieved. Certain x-ray detectors employing gaseous media have also incorporated grid structures in addition to the electrode structure shown in the above-mentioned patent, the grid structure acting to accelerate electron and ion drift so as to increase the response time of the detector.

Also, present airport security systems employ flying spot scanner type x-ray systems for the inspection of luggage. Such flying spot x-ray systems are also used to inspect food for the presence of foreign matter, such as glass fragments in baby food jars. In these systems, a rotating collimator, with holes near its periphery, causes an x-ray pencil beam to sweep across the object. The next collimator hole produces the next scan, the linear velocity of the object (for example, on a conveyor belt) being adjusted relative to that of the rotating collimator so that succeeding scans are essentially contiguous to each other. In such a system, a single detector is used which is used to produce a video signal in a television-like format, that is, as a sequence of more or less contiguous scan lines. The image may then be displayed on a cathode ray tube (CRT) or analyzed so as to detect the presence of irregularities, such as foreign matter in a food container.

However, flying spot x-ray scanners are not satisfactory if low noise data is required at a moderate scan rate at, say for example, more than 1,000 picture elements per second. At such high scan rates, the x-ray source intensity requirements become very severe or completely impossible. The reason for this is obvious in that such flying spot scanners yielding a 100×100 element image of an object requires 10,000 times the total source x-ray energy compared to a standard x-ray picture in which the entire image is exposed simultaneously. Thus, a typical flying spot x-ray scanning system might require as long as 10 seconds to produce a square 10,000 picture element image. This 1,000 picture element per second or less requirement implies a linear velocity for the object of only 1 cm per second, assuming a 1 mm×1 mm picture element resolution and a 10 cm×10 cm field of view. Such object velocities are highly unsatisfactory for detecting foreign objects in processed food made in high speed production runs.

Other x-ray inspection systems, having lower power requirements, are also built using conventional phosphor screens for x-ray detection. In these systems, the x-rays are pulsed to expose the entire image simultaneously. A TV pickup tube (such as a vidicon) is optionally coupled to the phosphor screen through a lens. The vidicon target integrates the light and is subsequently scanned by an electron beam to yield an image. Such systems have relatively low source power requirements and can yield images suitable for visual inspection. However, vidicon target imperfections, scan noise, and other noise sources make vidicon systems unsatisfactory when low noise is required, as for example, if one wants to detect changes in x-ray intensity of only a few percent. Such relatively small changes in x-ray intensity, however do occur, for example when a small (1 mm×1 mm) glass particle occurs in a baby food jar.

SUMMARY OF THE INVENTION

In accordance with a preferred embodiment of the present invention, an x-ray system particularly useful in airport luggage inspection or detection of foreign material in food packaging comprises an x-ray fan beam source directed at an object moving translationally through the fan beam, and an x-ray detector including a substantially planar power electrode and a plurality of substantially planar signal electrodes disposed within a gaseous detecting medium, such as xenon gas. The signal and power electrodes are maintained at relatively different voltage levels thereby causing charged particles generated within the gaseous medium between the electrodes to drift towards the electrodes and causing a signal current within each signal electrode, said current level being directly related to the x-ray intensity existing between each signal electrode and the power electrode.

Current sensing means operate to indicate the current level. These current signals may be amplified and differentiated, for example, by a passive resistance-capacitance network, and the resultant electrical pulses counted so as to indicate the presence and location of foreign material present. Alternatively, the signals produced by the detector of the x-ray scanning system may be employed to generate video image signals, for example, on a CRT.

DESCRIPTION OF THE DRAWINGS

FIG. 5 is a partial cross-sectional side elevation view of an x-ray scanning system of the present invention in which the electrodes possess parallelogram shapes with their long edges oriented parallel to the incident x-ray photon paths.

FIG. 6 is a partial cross-sectional side elevation view of an x-ray detector employed in a scanning system of the present invention in which the detector housing is curved and the electrodes are rectangular with their long edges oriented parallel to the incident x-ray photon paths.

FIG. 7 is a partial cross-sectional side elevation view illustrating the x-ray scanning system of the present invention being employed to detect foreign matter in a jar of baby food.

FIG. 8 is graph of x-ray intensity versus time for the signal current output corresponding to two of the signal electrode in FIG. 7.

FIG. 9 is a schematic view illustrating the use of signal processing circuits to indicate the detection of foreign matter within the object being scanned.

DETAILED DESCRIPTION OF THE INVENTION

Figure 1:
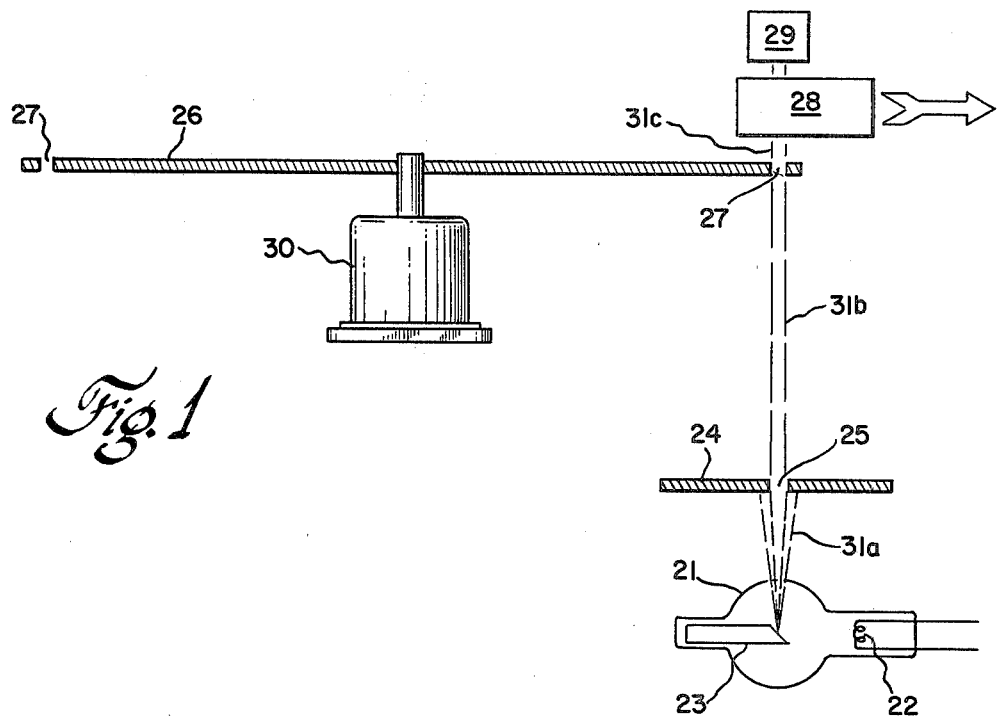
FIG. 1 is a partial cross-sectional top view illustrating the operation of a typical flying spot x-ray scanning system.

FIG. 1 illustrates a conventional flying spot scanner. X-ray tube 21 operates continuously by accelerating electrons from filament 22 toward anode 23 where they are suddenly decelerated, resulting in the production of a continuous x-ray photon beam 31a. X-ray beam 31a is shaped into a fan beam configuration by passage through collimator plate 24 typically comprising an x-ray opaque material such as lead, tungsten, or tantalum. Collimator plate 24 possesses a slit 25 from which x-ray fan beam 31b exits. X-ray fan beam 31b then impinges upon rotating collimator disk 26 driven by motor 30, said collimator disk possessing holes 27 near its periphery. Collimator 26 operates on fan beam 31b to produce a moving x-ray pencil beam 31c which scans object 28 which passes translationally through the fan beam as shown. After passage through the object 28, the x-ray beam impinges upon detector 29. The holes 27 in rotating disk 26 are typically selected to be uniformly distributed about the periphery of the disk 26, which is rotated by motor 30 at an angular velocity coordinated with the translational velocity of object 28 so that relatively contiguous portions of object 28 are scanned. Collimator disk 26 typically comprises material similar to that of collimator plate 24.

Figure 2:
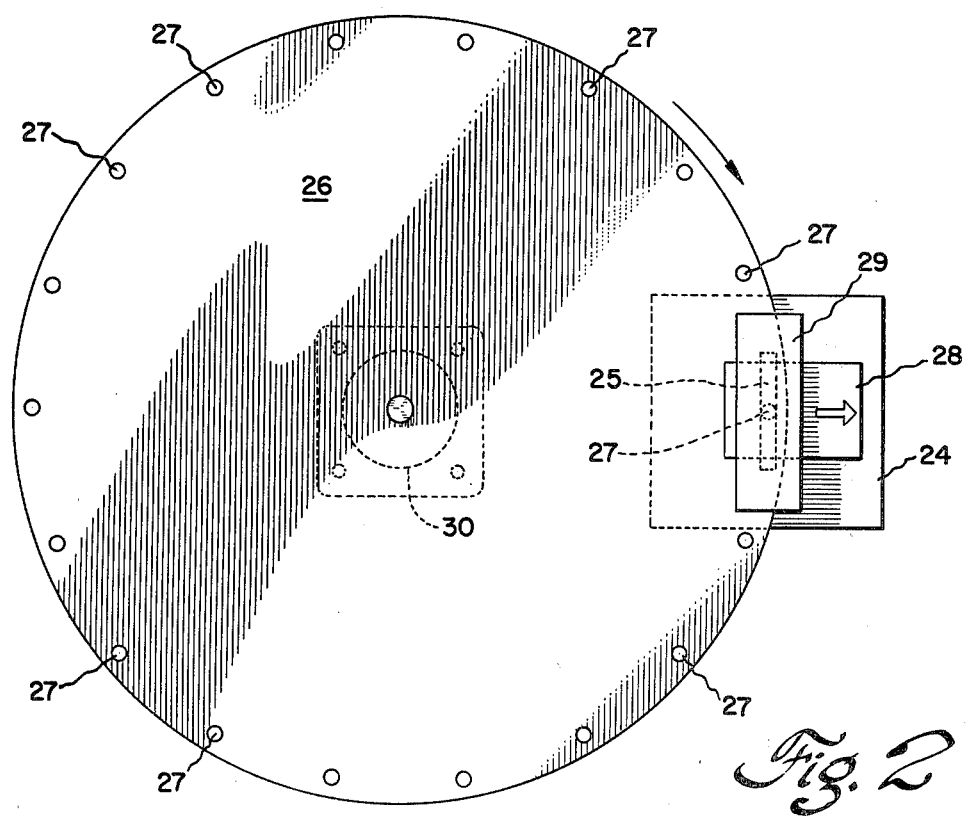
FIG. 2 is a side elevation view of the flying spot scanning system of FIG. 1.

FIG. 2 is a side view of the flying spot x-ray scanner system shown in FIG. 1. This view shows rotating collimator disk 26 with holes 27 from which the scanning pencil beam is emitted as each hole in the disk passes through the fan beam 31b shaped by collimator plate 24 possessing slit 25. The resulting pencil beam 31c passes through object 28 and impinges upon detector 29.

Figures 3, 4:
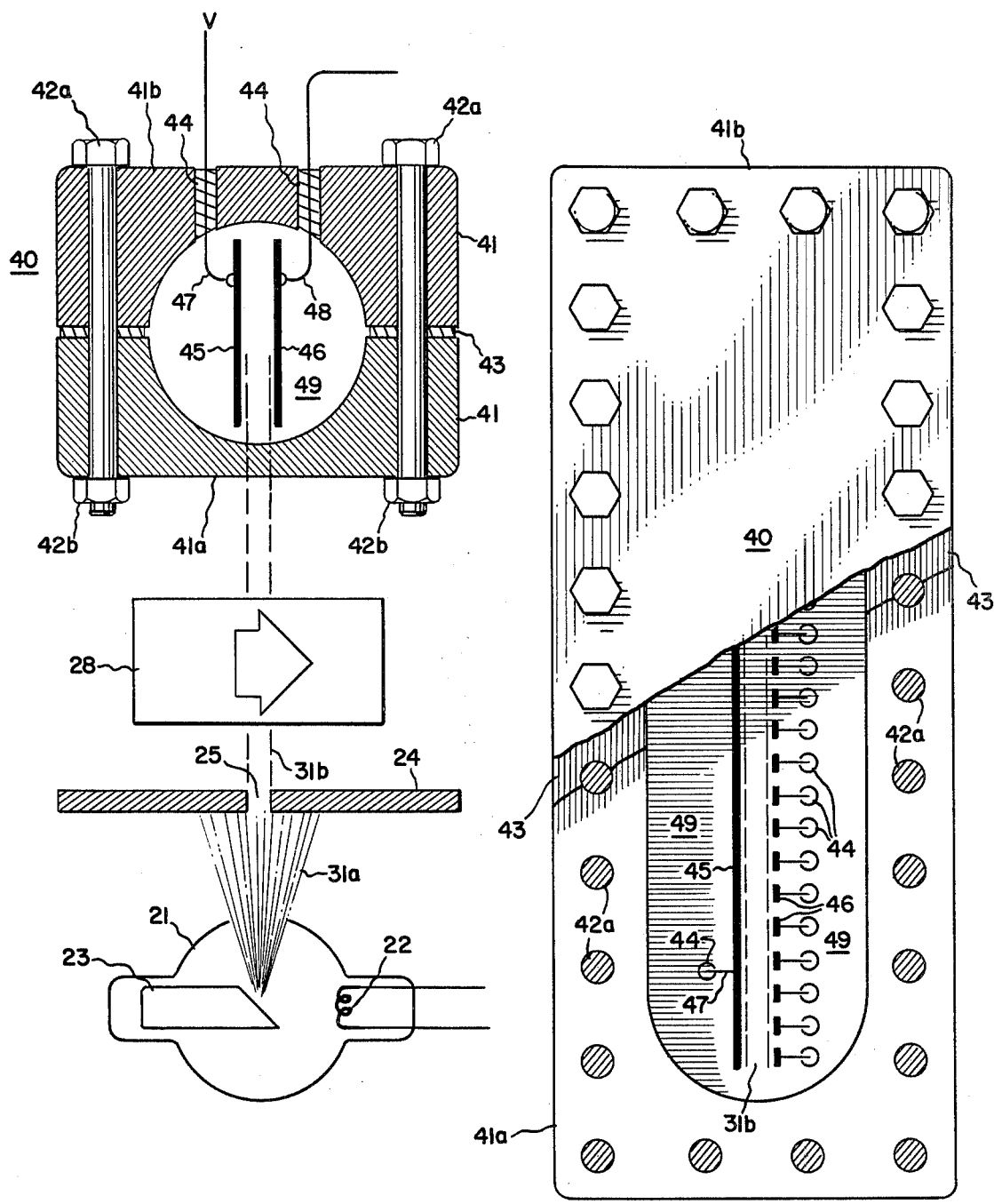
FIG. 3 is a partial cross-sectional top view of an x-ray system in accordance with a preferred embodiment of the present invention.
FIG. 4 is a partial cross-sectional side elevation view of the x-ray detector employed in the x-ray scanning system of the present invention.

FIG. 3 illustrates an x-ray scanning system in accordance with a preferred embodiment of the present invention which eliminates the need for a rotating collimator disk and provides advantages in requiring less energy for x-ray production, faster scan rates, low noise measurements, and high resolution. As in FIG. 1, x-ray tube 21 operates to produce x-ray emission 31a through the interactions of high voltage electrons from filament 22 with anode 23. X-ray beam 31a is shaped by collimator plate 24 possessing slit 25 thereby producing a fan-shaped x-ray beam 31b which passes through object 28 moving translationally through the fan beam, for example, by conveyor belt means. Object 28 absorbs various amounts of said x-ray beam depending upon its material composition. The x-ray beam is then made to impinge upon detector 40, said x-ray beam being modulated in intensity in direct correspondence with the absorbtivity of the various portions of object 28.

The use of a detector such as that shown in FIGS. 3 and 4 designated by reference numeral 40, significantly reduces the x-ray intensity level required in analyzing a single slice of object 28, as compared with the energy required in flying spot scanning systems. FIG. 3 shows a top sectional view of the detector 40 and FIG. 4 shows a partial sectional side elevation view of detector 40. The detector comprises a housing 41 preferably comprising an x-ray transmissive material such as aluminum. The detector contains an inner cavity in which is disposed a gaseous detecting medium 49 at a pressure between approximately 10 atmospheres and approximately 100 atmospheres. Gases usable in such a detecting medium include argon, krypton, and xenon and mixtures thereof, or other ionizable gaseous media having an atomic weight greater than the atomic weight of argon. However, a preferred embodiment of the present invention employs xenon gas at a pressure of approximately 25 atmospheres.

The detector housing is preferably constructed in two portions, a front portion 41a and a back portion 41b which are constructed so as to define a substantially cylindrical cavity for the containment of said gaseous detecting medium 49. Preferably, housing portion 41a possesses a thinner wall on that face oriented toward x-ray source 21. Such a construction minimizes x-ray absorption by the housing material itself, which is typically aluminum but may comprise any suitable atomically light weight x-ray transmissive material. Housing portions 41a and 41b are joined together by nuts 42b and bolts 42a with a gasket 43 preferably disposed between housing portions 41a and 41b so as to provide a gas-tight pressure seal. Within the cavity defined by housing portions 41a and 41b, are disposed power electrode 45 and signal electrodes 46. Power electrode 45 is a substantially planar electrode disposed essentially opposite and spaced apart from signal electrodes 46 which lie in a plane parallel to power electrode 45 which is preferably maintained at a high voltage V with respect to said signal electrodes 46. Said power electrode 45 and said signal electrodes 46 are externally connected electrically by means of wire leads 47 and 48 respectively passing through openings in housing 41, said openings typically being filled with an electrically insulative material 44, such as an epoxy or silicone resin. Power electrode 45 is externally connected electrically through lead 47 and signal electrodes 46 are connected externally by means of wire leads 48. Additional leads at the same potential as lead 47 may also be used to provide additional mechanical support for power electrode 45. Alternately, the leads are brought out through gasket 43. Signal electrodes 46 are preferably operated essentially at ground potential thereby eliminating any necessity for guard rings between each signal electrode. Alternatively, the signal electrodes 46 may comprise a plurality of metal strips bonded to the surface of a dielectric sheet and applied to the sheet in any conventional manner, for example, screen printing, etching laminated printed circuit board material, or vapor deposition. The dielectric sheet may, for example, comprise reinforced epoxy resin, ceramic, or any other material commonly used for that purpose in detector arts. The electrodes 45 and 46 are spaced apart and oriented so that x-ray fan beam 31b passes between said electrodes and thus acts to ionize the gaseous detecting medium 49 disposed between said power electrode 45 and said signal electrodes 46. The gas type, gas pressure, electrode length, and spacing between the electrodes are chosen using methods well known to the art so that a large fraction, typically more than 70 percent, of the incident x-ray photons are absorbed within the gas. In the present invention, the spacing between adjacent signal electrodes 46 and also between power electrode 45 and signal electrodes 46 is determined by the desired resolution of the x-ray system.

Incident x-rays interact with the gaseous detecting medium 49 disposed between the power electrode 45 and the signal electrodes 46 to produce electron-ion pairs. The electrons drift under the influence of the electric field imposed by the voltage V on the power electrode 45, while the ions are similarly collected on the signal electrodes 46. Current flow in the signal electrodes is proportional to the number of interactions between photons and gas atoms in the region between the power electrode 45 and the signal electrodes 46 so that the current distribution among the individual signal electrodes 46 is a function of the distribution of the x-ray intensity along the detector array. The direction of electron and ion motion within the detector is substantially perpendicular to the array length and to the direction of incident x-ray photons.

In the present invention, the x-ray source 21 operates continuously. Each signal electrode 46 thus yields a changing video signal as the object 28 moves translationally past the detector. These video signals are typically relatively slow-varying due to the time constant of the detector which is approximately 1 millisecond in the case that the detecting gaseous medium 49 is xenon at a pressure of approximately 25 atmospheres. However, if desired, a faster response time is achieved by utilizing only the electrons produced in the interaction between the x-rays and the gaseous medium. This increased response time is achieved by the use of a grid maintained at a voltage level intermediate the level of the power and signal electrodes. For example, such grid structures are described in U.S. Pat. No. 4,047,041 issued Sept. 6, 1977 to the applicant herein, which patent is also incorporated herein by reference.

The video signals may be time sampled, using well known techniques, and displayed as a TV signal on a CRT. However, normally one would merely differeniate each video signal and observe sudden changes in x-ray absorption, such as would be caused by some foreign object, for example, a piece of glass or metal. Fortunately, most foods, potentially containing such foreign matter, are rather homogenous, and liquid-filled foods, such as canned fruit and vegetables have an x-ray absorption very similar to that of water.

Because the x-ray source should not be distant from the food being inspected so as to maintain x-ray intensity at minimum levels, parallax effects exist but these may be readily compensated for by aiming the signal electrodes at the x-ray source so as not to lose spatial resolution particularly when scanning near the top and bottom of the object. FIG. 5 illustrates a preferred detector construction in which such aiming occurs. In FIG. 5, detector 40 still employs a substantially rectangular housing. However, the signal electrodes in FIG. 5 comprise parallelograms whose long edges are radially oriented with respect to the x-ray source 21, so as each signal electrode 46 remains parallel to the direction of incident x-ray photons. Alternatively, the detector housing may be curved as shown in FIG. 6, where the signal electrodes 46 comprise rectangles disposed along an arc and oriented radially with respect to the x-ray source. However, the housing and pressure gaskets are much easier to fabricate if the structure is kept planar.

FIG. 7 illustrates the detector of the present invention employed to detect foreign matter within a jar of processed food, for example, baby food. The jar 60 containing substance 61 and lid 63 travels as shown thus exhibiting a leading wall edge 60a and a trailing wall edge 60b. Foreign matter 62, for example a glass particle, is suspended within substance 61, which might comprise food matter, such as baby food. Detector 40 is shown with power electrode 45 and signal electrodes 46, with signal electrodes 46a and 46b being particularly singled out as being an electrode not within the path of foreign particle 62 and an electrode being within the path of foreign particle 62, respectively.

FIG. 8 represents a plot of the x-ray intensity as measured by the current levels in signal electrodes 46a and 46b as measured versus time. Curve portion AC'B represents the signal produced at electrode 46a; Curve portion ACB represents the signal level at electrode 46b. In both cases, curve portion A and curve portion B represent relatively sharp drops in x-ray intensity occurring as the result of the passage of leading container wall 60a and trailing container wall 60b, respectively. However, curve portions C and C' in FIG. 8 differ. Curve portion C indicates a relatively sharp drop in x-ray intensity as the result of the passage of foreign particle 62 through the x-ray fan beam. Such differences between the two curves may be readily observed to detect the presence of foreign matter. Additionally, as shown in FIG. 9, detector 40 may be employed in conjunction with preamplification circuitry 70, a differentiator 72, and a counter 74 for the automatic detection of such foreign particles or matter. Other signal processing apparatus as is well known in the signal processing art, may also be advantageously employed. Such apparatus may also include differentiators, half-wave rectifiers, amplifiers, limiters, filters, and counters. As is suggested in FIG. 9, the signal processing circuitry may be attached to each individual signal electrode or may be time shared between all the signal electrodes or groups of signal electrodes.

By way of example, and not limitation, an x-ray scanning system of the present invention for inspecting jars of baby food, 4 inches (100 mm) high and 2.5 inches (64 mm) in diameter might be describable by the following system parameters: detector array height equals 110 mm; signal electrode periodicity equals 1 mm; the number of signal electrodes and preamplifiers equals 110; the gap between power electrode and signal electrodes equals 2 mm; size of the x-ray fan beam at jar centerline equals 110 mm high×1 mm wide; the length of signal and power electrodes in the direction of the x-ray beam equals 10 mm; xenon pressure equals 40 atmospheres; distance from x-ray source to jar centerline equals 30 cm. The signal electrode periodicity and fan beam width determine the picture element size, which in this case is 1 mm×1 mm; each picture element is scanned for 1 millisecond, said time being determined by the detector response time, and the corresponding conveyor belt speed is 1 meter per second, corresponding to scanning 15 jars of food per second. Slower speeds, of course, cause no problem.

At typical x-ray voltages (that is, 120 kvp), the average x-ray photon energy is approximately 60 kev. An x-ray beam of this energy is attenuated by a factor of 3.6 in passing through 2.5 inches of watery food. A sliver of glass 1 mm thick (in the x-ray direction) causes an intensity change of 3.3 percent. In order to detect this change easily, the x-ray quantum noise must be an order of magnitude smaller, that is approximately 0.3 percent. Since fluctuation noise equals $1/\sqrt{N}$, where N is the number of x-ray photons this level of noise requires that approximately $10^5$ x-ray photons be absorbed by the detector per picture element. Since, in the above example, the scanning time per picture element is 1 millisecond, the detector must detect $10^8$ photons per second. A detector quantum efficiency of 50 percent, and an attenuation in the food of 3.6, and a source to jar distance of approximately 30 cm, all imply an x-ray source operting at a continuous electrical power of 1.2 kw. This is well within the capability of current off-the-shelf continuous x-ray sources which are available up to approximately 4 kw.

From the above, it can be appreciated that the x-ray scanning system and detector of the present apparatus provide a system particularly suitable for detecting foreign matter in food and additionally for generating video images for display as in airport luggage inspection systems. The present invention is superior to conventional flying spot systems in that no rapidly rotating collimator is required and x-ray source power requirements are reduced by several orders of magnitude. Additionally, as compared to a vidicon plus phosphor screen system, the present invention achieves a much lower noise level rendering it capable of detecting changes of only a few percent in x-ray absorption.

While this invention has been described with reference to particular embodiments and examples, other modifications and variations will occur to those skilled in the art in view of the above teachings. Accordingly, it should be understood that the appended claims are intended to cover all such modifications and variations as fall within the spirit of the invention.

The invention claimed is:

1. An x-ray scanning system for generating signals corresponding to x-ray absorption levels in an object comprising:
   means for translationally moving said object;
   x-ray means for subjecting said object to a substantially flat, fan-shaped x-ray beam, said beam being in a plane which does not contain the direction of motion of said object;
   a detector, said detector having a substantially planar power electrode and a plurality of substantially planar signal electrodes spaced apart from and parallel to said power electrode, said signal electrodes being configured so as to lie in a plane substantially parallel to said power electrode, said power electrode and said signal electrodes being parallel to the plane of said fan-shaped x-ray beam and positioned so that said beam passes between said power electrode and said signal electrodes, all of said electrodes being disposed in an x-ray transmissive housing containing a gaseous detecting medium;
   means to impress a voltage on said power electrode relative to said signal electrodes;
   means to sense current passing through each of said signal electrodes.

2. The x-ray scanning system of claim 1 in which said x-ray means comprises:
   a source of x-rays; and
   a collimator sheet having a slit, said collimator being positioned between said x-ray source and said object so as to subject said object to a substantially flat, fan-shaped x-ray beam, said beam being in a plane which does not contain the direction of motion of said object.

3. The x-ray scanning system of claim 1 in which the signal electrodes are parallel, one to the other.

4. The x-ray scanning system of claim 1 in which said gaseous detecting medium comprises substances of atomic weight greater than or equal to the atomic weight of argon.

5. The x-ray scanning system of claim 1 in which said gaseous medium comprises material selected from the group consisting of argon, krypton, xenon, and mixtures of argon, krypton, and xenon.

6. The x-ray scanning system of claim 1 in which said gaseous detecting medium has a pressure between approximately 10 atmospheres and approximately 100 atmospheres.

7. The x-ray scanning system of claim 1 in which said signal electrodes comprise strips of electrically conductive material disposed on a sheet of dielectric material.

8. The x-ray scanning system of claim 1 in which said housing is circularly arcuate and said signal electrodes having a long dimension lying substantially along the radii of said circular arc.

9. The x-ray scanning system of claim 1 in which said housing comprises aluminum.

10. The x-ray scanning system of claim 1 in which said signal electrodes are parallelograms with a long dimension oriented substantially parallel to the incident direction of said fan beam.

* * * * *